United States Patent
Zhang et al.

(10) Patent No.: US 10,982,869 B2
(45) Date of Patent: Apr. 20, 2021

(54) INTELLIGENT SENSING SYSTEM FOR INDOOR AIR QUALITY ANALYTICS

(71) Applicant: Board of Trustees of Michigan State University, East Lansing, MI (US)

(72) Inventors: Mi Zhang, Okemos, MI (US); Biyi Fang, East Lansing, MI (US); Taiwoo Park, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 187 days.

(21) Appl. No.: 15/700,492

(22) Filed: Sep. 11, 2017

(65) Prior Publication Data

US 2018/0073759 A1    Mar. 15, 2018

Related U.S. Application Data

(60) Provisional application No. 62/393,713, filed on Sep. 13, 2016.

(51) Int. Cl.
| | |
|---|---|
| *F24F 11/30* | (2018.01) |
| *G01N 33/00* | (2006.01) |
| *G05B 19/042* | (2006.01) |
| *G05B 17/02* | (2006.01) |
| *F24F 110/70* | (2018.01) |
| *F24F 110/50* | (2018.01) |

(Continued)

(52) U.S. Cl.
CPC .......... *F24F 11/30* (2018.01); *G01N 33/0075* (2013.01); *G05B 17/02* (2013.01); *G05B 19/042* (2013.01); *F24F 11/62* (2018.01); *F24F 2110/10* (2018.01); *F24F 2110/20* (2018.01); *F24F 2110/50* (2018.01); *F24F 2110/64* (2018.01); *F24F 2110/65* (2018.01); *F24F 2110/66* (2018.01); *F24F 2110/70* (2018.01); *G01N 33/0004* (2013.01); *G05B 2219/2642* (2013.01)

(58) Field of Classification Search
None
See application file for complete search history.

(56) References Cited

U.S. PATENT DOCUMENTS

| | | | | |
|---|---|---|---|---|
| 4,603,575 A | * | 8/1986 | Rahn ................... | G01N 33/0075 436/56 |
| 5,112,455 A | * | 5/1992 | Cozzette ............ | G01N 27/3274 205/778 |

(Continued)

OTHER PUBLICATIONS

S. Kim et al "inAir: Sharing Indoor Air Quality Measurements and Visualizations" CHI 2010, Atlanta, GA (2010).

(Continued)

*Primary Examiner* — Catherine T. Rastovski
*Assistant Examiner* — Leonard S Liang
(74) *Attorney, Agent, or Firm* — Harness, Dickey & Pierce, PLC

(57) ABSTRACT

Existing indoor air quality monitoring technologies focus on measuring which turn out to be effective in increasing people's awareness of air quality. However, the lack of identification of pollution sources is prone to lead to general and monotonous suggestions. In this disclosure, an indoor air quality analytics system is presented that is able to detect pollution events and identify pollution sources in real-time. The system can also forecast personal exposure to air pollution and provide actionable suggestions to help people improve indoor air quality.

19 Claims, 12 Drawing Sheets

(51) Int. Cl.

| | |
|---|---|
| *F24F 110/66* | (2018.01) |
| *F24F 110/20* | (2018.01) |
| *F24F 110/10* | (2018.01) |
| *F24F 110/64* | (2018.01) |
| *F24F 110/65* | (2018.01) |
| *F24F 11/62* | (2018.01) |

(56) References Cited

U.S. PATENT DOCUMENTS

| | | | | |
|---|---|---|---|---|
| 9,317,732 | B2* | 4/2016 | Gong | G06K 9/00 |
| 9,890,969 | B2* | 2/2018 | Martin | G01N 33/00 |
| 10,222,360 | B1* | 3/2019 | Nourbakhsh | G01N 33/0075 |
| 10,359,280 | B2* | 7/2019 | Bai | |
| 2001/0005130 | A1* | 6/2001 | Manzini | G01N 33/205 |
| | | | | 324/71.4 |
| 2004/0049297 | A1* | 3/2004 | Card | G05B 13/027 |
| | | | | 700/28 |
| 2004/0168108 | A1* | 8/2004 | Chan | G05B 23/0254 |
| | | | | 714/47.1 |
| 2004/0213446 | A1* | 10/2004 | Shams | G06T 7/0012 |
| | | | | 382/129 |
| 2004/0226354 | A1* | 11/2004 | Schmidt | G01N 33/0018 |
| | | | | 73/114.73 |
| 2006/0036345 | A1* | 2/2006 | Cao | G05B 13/024 |
| | | | | 700/108 |
| 2007/0269770 | A1* | 11/2007 | Pellegrino | G08B 21/12 |
| | | | | 434/15 |
| 2007/0294060 | A1* | 12/2007 | Pellegrino | G08B 31/00 |
| | | | | 702/190 |
| 2009/0222321 | A1* | 9/2009 | Liu | G06F 16/951 |
| | | | | 705/7.31 |
| 2011/0218454 | A1* | 9/2011 | Low | A61B 5/0476 |
| | | | | 600/544 |
| 2012/0290230 | A1* | 11/2012 | Berges Gonzalez | |
| | | | | G05B 19/0428 |
| | | | | 702/61 |
| 2013/0174646 | A1* | 7/2013 | Martin | G01N 33/00 |
| | | | | 73/31.02 |
| 2015/0096352 | A1* | 4/2015 | Peterson | F24F 11/30 |
| | | | | 73/31.02 |
| 2015/0117767 | A1* | 4/2015 | Gong | G06K 9/00 |
| | | | | 382/160 |
| 2015/0154504 | A1* | 6/2015 | Zhang | G06N 7/005 |
| | | | | 706/52 |
| 2015/0164339 | A1* | 6/2015 | Xu | A61H 31/005 |
| | | | | 600/324 |
| 2016/0089080 | A1* | 3/2016 | Li | A61B 5/1123 |
| | | | | 702/141 |
| 2016/0305678 | A1* | 10/2016 | Pavlovski | G05B 13/048 |
| 2016/0313023 | A1* | 10/2016 | Przybylski | F24F 11/30 |
| 2016/0314256 | A1* | 10/2016 | Su | G06F 19/3462 |
| 2016/0371181 | A1* | 12/2016 | Garvey | G06F 12/0253 |
| 2017/0016644 | A1* | 1/2017 | Nagarathinam | G05B 19/0428 |
| 2017/0108236 | A1* | 4/2017 | Guan | G05B 15/02 |
| 2017/0108511 | A1* | 4/2017 | Parekh | G01N 33/6893 |
| 2017/0123440 | A1* | 5/2017 | Mangsuli | F24F 11/30 |
| 2017/0351288 | A1* | 12/2017 | Li | G05B 13/0265 |
| 2018/0073759 | A1* | 3/2018 | Zhang | G01N 33/0075 |
| 2018/0119973 | A1* | 5/2018 | Rothman | F24F 11/62 |
| 2018/0236352 | A1* | 8/2018 | El-Sheimy | G06F 3/011 |
| 2018/0239057 | A1* | 8/2018 | Bai | G01W 1/10 |
| 2018/0245913 | A1* | 8/2018 | Radai | G06F 3/0346 |
| 2018/0313649 | A1* | 11/2018 | Bai | G01N 33/00 |
| 2019/0017721 | A1* | 1/2019 | Motodani | F24F 11/63 |
| 2019/0175077 | A1* | 6/2019 | Zhang | A61B 5/7475 |
| 2019/0257543 | A1* | 8/2019 | Martin | F24F 11/30 |

OTHER PUBLICATIONS

Y. Kobayashi et al "A Context Aware System Based on Scent", 2011 IEEE, 15th Annual International Symposium on Wearable Computers (2011).

Y. Jiang et al "MAQS: A Personalized Mobile Sensing System for Indoor Air Quality Monitoring", UbiComp'11/Beijing, China (2011).

Y. Cheng et al "AirCloud: A Cloud-based Air-Quality Monitoring System for Everyone", SenSys'14, Memphis, TN (2014).

X. Chen et al "Indoor Air Quality Monitoring System for Smart Buildings" UbiComp '14, Seattle, WA (2014).

\* cited by examiner

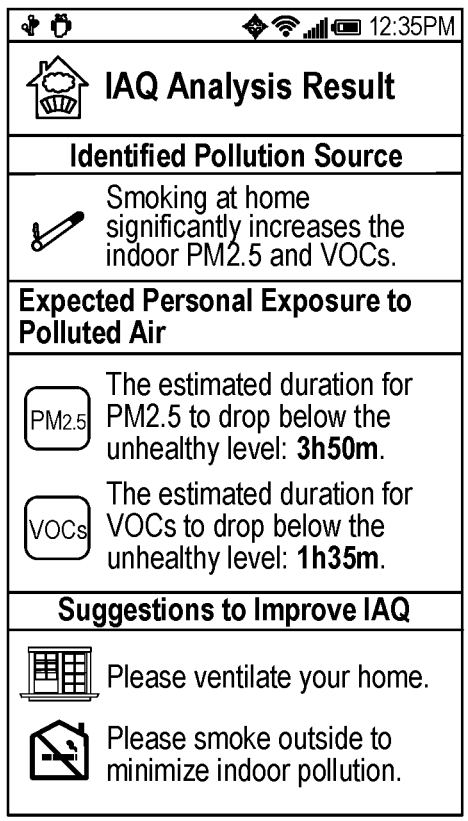
FIG. 10A
FIG. 10B
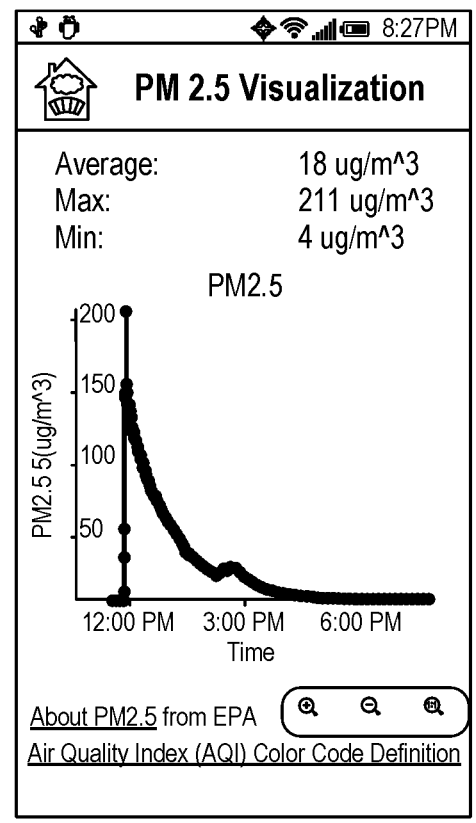

INTELLIGENT SENSING SYSTEM FOR INDOOR AIR QUALITY ANALYTICS

CROSS-REFERENCE TO RELATED APPLICATIONS

This application claims the benefit of U.S. Provisional Application No. 62/393,713, filed on Sep. 13, 2016. The entire disclosure of the above application is incorporated herein by reference.

FIELD

The present disclosure relates to an intelligent sensing system for indoor air quality analytics.

BACKGROUND

Indoor air quality (IAQ) plays a significant role in our daily lives. In the United States, people spend approximately 90 percent of their time indoors, consuming about 3400 gallons of air on average every day. Unfortunately, according to Environmental Protection Agency (EPA), indoor air pollution may be two to five times—and on occasion more than 100 times—worse than the air outdoors. Poor IAQ could pose significant risks to people's health and is the leading cause of respiratory infections, chronic lung diseases, and cancers. Therefore, IAQ is ranked as one of the EPA's top five environmental risks to public health.

Although we are potentially exposed to such an amount of air pollution at home, IAQ is often overlooked for two major reasons. First, although some of the indoor air pollutants like formaldehyde have irritating odor, the majority of them is colorless, odorless, or too tiny to see. This makes indoor air pollutants almost impossible to be perceived by human beings. Second, many adverse health conditions caused by indoor air pollution such as cancer have no severe symptoms until years after long period of exposure. For immediate adverse health effects, some of them such as coughs and headaches are very similar to symptoms of colds or other viral diseases. Therefore, it is very difficult to determine whether the symptoms are results of exposure to indoor air pollutants.

Due to its critical role in health and wellbeing, IAQ has attracted considerable attention in the ubiquitous computing community in recent years. Pioneer works focused on developing IAQ monitoring systems for visualizing IAQ-related measures. Although those systems increased users' awareness of IAQ, they did not provide identification of pollution sources as well as any estimation of how long the pollution will stay. Without that critical information, users can only understand the overall IAQ vaguely. As a consequence, users are unlikely to realize the seriousness of pollution and take proper actions. The lack of information about the pollution sources, the estimate of the seriousness of the pollution as well as the specific suggestions to help reduce the immediate indoor air pollution make people feel powerless and frustrated, leading to the ignorance of the IAQ-related measures provided by the IAQ monitoring systems.

In this disclosure, this critical gap is bridged by developing an intelligent indoor air quality sensing system that is capable of automatically detecting indoor air pollution events, identifying pollution sources, forecasting future IAQ information to estimate the expected personal exposure to indoor air pollution, and provide specific suggestions to help people improve IAQ in a timely manner. The proposed air quality sensing system (referred to herein as AirSense) is developed upon commercial off-the-shelf air quality sensors to continuously monitor the ambient temperature, humidity and the concentrations of particulates (PM) and volatile organic compounds (VOC) which are two of the most common indoor air pollutants. The proposed air quality sensing system detects air pollution events and then identifies air pollution sources of the events by analyzing the real-time sensor data. Based on the identified pollution sources, the sensing system predicts the IAQ in the near future to estimate the expected personal exposure to indoor air pollution. To minimize users' exposure to indoor air pollution, the proposed air quality sensing system provides specific suggestions based on the pollution source, level and degree of harmfulness to help users reduce indoor air pollution in a timely manner. Finally, the proposed air quality sensing system provides a detailed weekly IAQ profile, which helps people better understand how household activities impact IAQ and identify household activities that pollute air the most.

Equipped with both monitoring and analytics capabilities, AirSense would be very helpful for people who are sensitive to air quality. Although currently designed for home uses, AirSense can be extended and find its applications in public buildings, such as office rooms, shopping malls and subway stations. AirSense can be used as a replacement for the smoke detectors currently installed in homes and public buildings, to provide indoor air quality monitoring and analytics services beyond simple smoke detection and fire alarming.

This section provides background information related to the present disclosure which is not necessarily prior art.

SUMMARY

This section provides a general summary of the disclosure, and is not a comprehensive disclosure of its full scope or all of its features.

A method is presented for identifying source of a pollution event in an indoor setting. The method includes: receiving a signal from a particulate matter sensor in the indoor setting; detecting a pollution event from the signal; extracting features proximate to the pollution event, where the features are extracted from the signal in response to detecting the pollution event; constructing a feature vector using the extracted features; comparing the feature vector to a plurality of pollution source models, where each pollution source model represents a different pollution event and identifies a source for the pollution event; and identifying a source of the pollution event based on the comparison of the feature vector with the plurality of pollution source models. Example sources for the pollution event include cooking, smoking and spraying pesticides.

In one embodiment, the pollution events are detected by detecting a peak in the signal and correlating the peak in the signal to a current pollution event. The peak in the signal may be detected by computing a standard deviation of values of the signal over a window of time, where the peak in the signal aligns with a maximum value of the standard deviation and a magnitude of the peak in the signal exceeds a threshold. Features for the feature vector are in turn extracted within a window of time, such that the window of time is centered about the peak in the signal. Example features include: increasing rate between the peak and a first data point in the window of time, a difference between the peak and the first data point in the window of time, a decreasing rate between the peak and a last data point in the window of time, a difference between the peak and the last data point in the window of time, and a standard deviation of all data points in the window of time.

In some embodiments, the method further includes receiving a second signal from at least one of a humidity sensor or a volatile organic compound sensor; and extracting features proximate to the pollution event from the second signal in response to detecting the pollution event.

In response to detecting the pollution event, the method may also include notifying a person of the pollution event, where the notification includes the identified source of the pollution event.

In other embodiments, the method includes forecasting amount of pollution in the indoor setting at a future time, where the forecasting is in response to detecting the pollution event.

In another aspect, a system is presented for sensing air quality in an indoor setting. The system includes one or more sensors, a data store and an analytics engine. For example, a particulate matter sensor is configured to measure concentration of particulates and VOC as well as humidity and temperature respectively in the indoor setting. The data store stores a plurality of pollution source models, where each pollution source model in the data store represents a different pollution event and identifies a source for the pollution event. The analytics engine is configured to receive a signal from the particulate matter sensor and is interfaced with the data store. In operation, the analytics engine detects a pollution event from the signal, extracts features from the signal in response to detecting the pollution event, and constructs a feature vector using the extracted features. The analytics engine also compares the feature vector to the plurality of pollution source models in the data store and identifies a source of the pollution event based on the comparison of the feature vector with the plurality of pollution source models, where the analytics engine is implemented by computer readable instructions executed by a computer processor.

In some embodiments, the system includes a humidity sensor, a temperature sensor and/or a volatile organic compound sensor.

In other embodiments, the system may include a forecaster that determines an amount of pollution in the indoor setting at a future time or a reporter that generates notifications for the pollution event.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 10A-10D depict example screens for the air quality sensing and analytics system.

Corresponding reference numerals indicate corresponding parts throughout the several views of the drawings.

DETAILED DESCRIPTION

Example embodiments will now be described more fully with reference to the accompanying drawings.

Figure 1A:
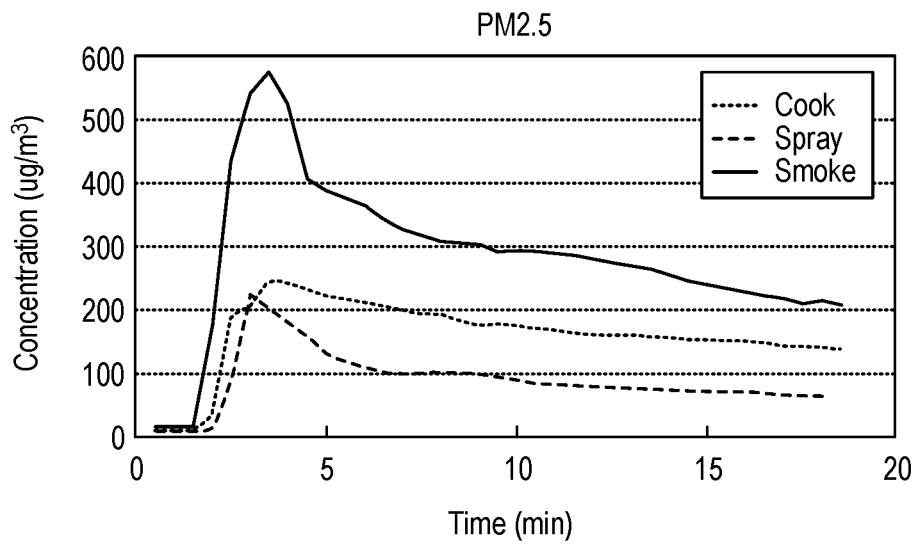
FIGS. 1A-1C are graphs depicting sensor measurements of indoor air pollution generated by cooking, smoking and spraying pesticide from (a) a particulate matter sensor, (b) a humidity sensor, and (c) VOC sensor, respectively.
Figure 1B:
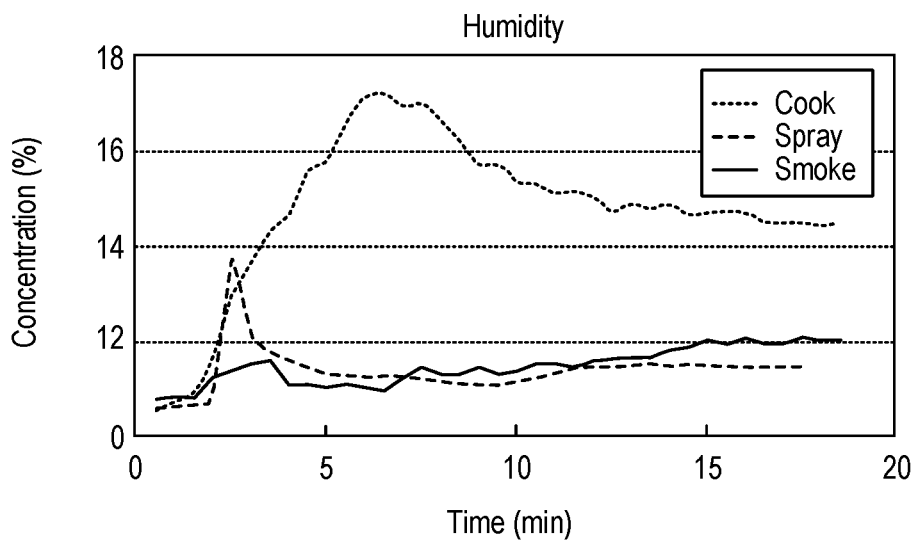
Figure 1C:
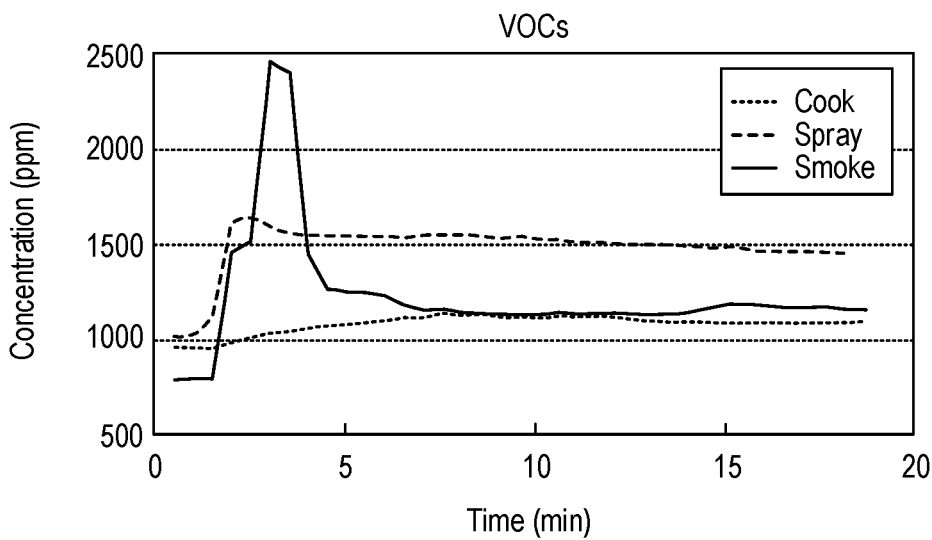

FIGS. 1A-1C illustrate sensor measurements from a particulate matter sensor, a humidity sensor, and a VOC sensor, respectively, of indoor air pollution generated by three household events: cooking, smoking, and spraying pesticide. Due to space limitation, FIG. 1 visualizes the measurements of about 20 minutes starting from the beginning of the events.

The development of an air quality sensing system is motivated by two key observations from FIG. 1. First, major air pollution sources such as cooking, smoking, and spraying pesticide lead to unique changes in particulates (e.g., PM 2.5), volatile organic compounds (VOC), and humidity levels. This motivates one to leverage these measures to detect indoor air pollution. For example, it is known that cooking, smoking and spraying pesticide all generate particles with a diameter of 2.5 μm or less (PM 2.5). As shown in FIG. 1A, there is a sharp increase in concentration of particulates at the beginning of these three events. This indicates that a particulate matter sensor may be useful in detecting these pollution events.

Second, there are patterns embedded in the sensor measurements that can be used to differentiate these three events.

This motivates one to develop pattern recognition and classification algorithms to recognize pollution sources from sensor measurements. For example, the humidity level changes only 1% for smoking while it increases about 7% for cooking as seen in FIG. 1B. As another example, the decreasing rate after the peak value of cooking is slower than the decreasing rate of both smoking and spraying pesticide as seen in FIG. 1A. One can leverage these patterns to build classification models for identifying these pollution sources.

Figure 2:
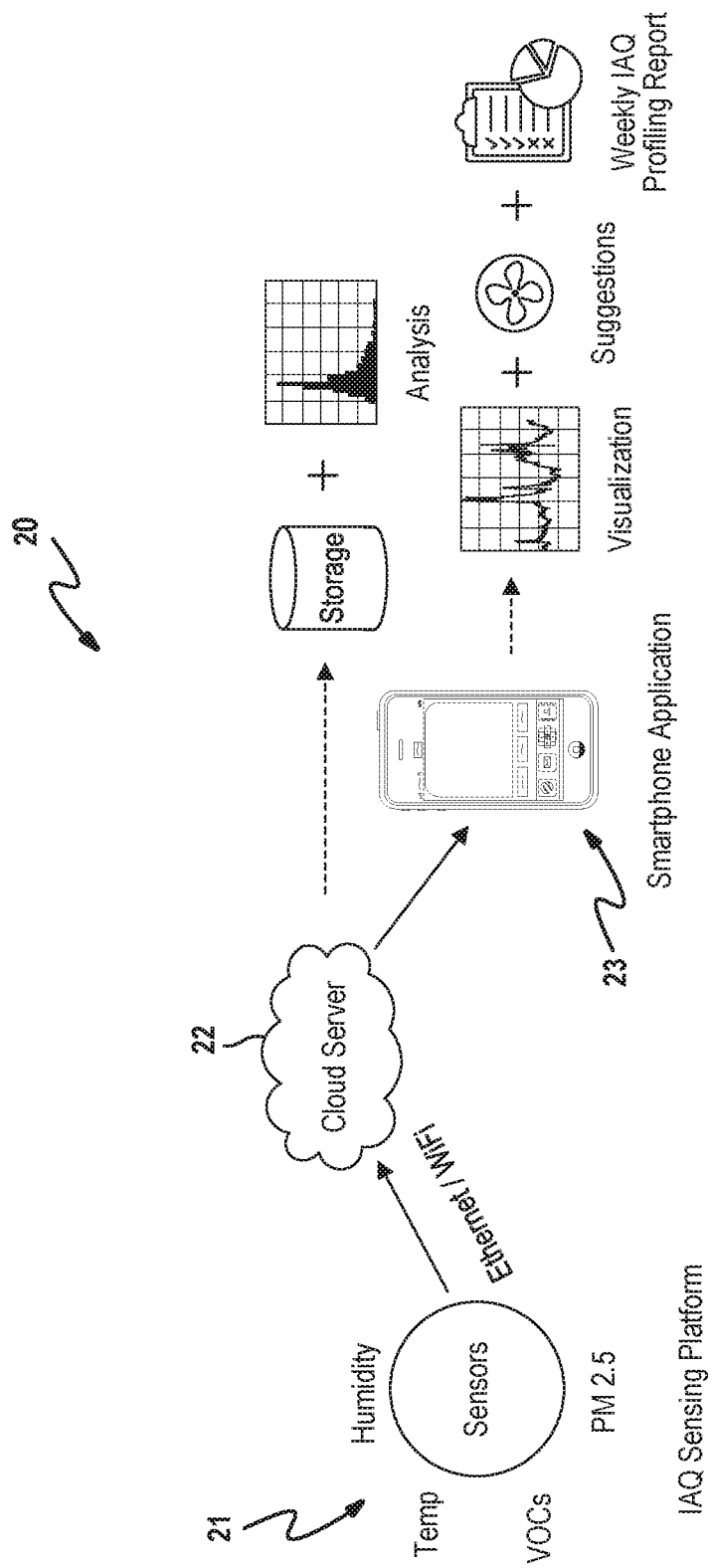
FIG. 2 is a diagram depicting an overview of a proposed system architecture for an air quality sensing and analytics system.

FIG. 2 provides an overview of an example system architecture for the AirSense air quality sensing system 20. As illustrated, the AirSense air quality sensing system 20 is comprised generally of three components: an IAQ sensing platform 21, a cloud server 22 and a delivery application which resides on a computing device 23, such as smartphone, a wearable device (e.g., a smart watch or a smart glasses), a tablet, or desktop computer. The IAQ sensing platform 21 collects data regarding the air quality of an indoor setting as will be further described below. The cloud server 22 stores the collected data in a database. In some embodiments, the cloud server 22 may also contains an analytics engine that analyzes the data. The analytics engine is able to detect the occurrences of indoor air pollution events, identify the sources of the pollution events, and forecast the air quality to estimate the expected personal exposure to indoor air pollution. In other embodiments, the analytics engine resides on the IAQ sensing platform 21 and performs these functions locally. In either case, the analytics engine can also generate suggestions that are specific to the identified pollution sources and then notify the user via the delivery application 23 so that the user could follow the suggestions to reduce indoor air pollution in a timely manner. Finally, a weekly IAQ profiling report can be generated weekly which summarizes the amount of indoor air pollution produced by pollution events.

Figure 3:
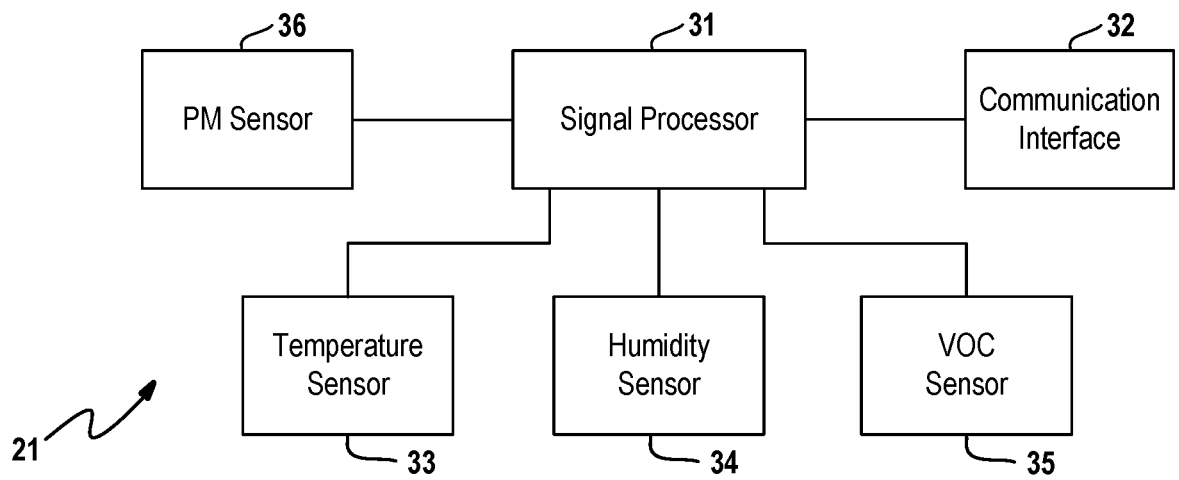
FIG. 3 is a block diagram of an example IAQ sensing and analytics platform.

Referring to FIG. 3, the IAQ sensing platform 21 is comprised of a signal processor 31, a communication interface 32 and one or more sensors. Logic of the signal processor can be implemented in hardware logic, software logic, or a combination of hardware and software logic. In an exemplary embodiment, the signal processor 31 is implemented as a microcontroller. In other embodiments, the signal processor 31 can be or can include any of a digital signal processor (DSP), microprocessor, microcontroller, or other programmable device which are programmed with software implementing the above described methods. It should be understood that alternatively the signal processor is or includes other logic devices, such as a Field Programmable Gate Array (FPGA), a complex programmable logic device (CPLD), or application specific integrated circuit (ASIC). When it is stated that the signal processor 31 performs a function or is configured to perform a function, it should be understood that signal processor 31 is configured to do so with appropriate logic (such as in software, logic devices, or a combination thereof).

In one embodiment, the IAQ sensing platform 21 includes a temperature sensor 33, humidity sensor 34, a volatile organic compound (VOC) sensor 35, and a particulate matter (PM 2.5) sensor 36. More or less sensors as well as other types of air quality sensors (e.g., smoke sensors) are contemplated by this disclosure.

In an example embodiment, the IAQ sensing platform 21 was developed on top of the Arduino Uno Ethernet board. The platform is equipped with three onboard sensors including temperature, humidity and VOCs sensors. Sampled sensor data is transmitted to the cloud server 22 via a communication interface (e.g., an onboard Ethernet port). In addition to the onboard sensors, the IAQ sensing platform 21 incorporates a standalone consumer-grade particulate matter (PM) sensor (e.g., DC 1700 from Dylos) to measure the concentration of indoor PM 2.5. In other embodiments, the sampled sensor data may be transmitted wirelessly to the cloud server, for example via WiFi, Bluetooth, or Cellular networks. The sampling rate of all the sensors is set to one sample per five seconds. Table 1 summarizes the air quality sensors.

TABLE 1

| Air Quality Sensor | Manufacturer |
|---|---|
| Particulate Matter (PM 2.5) | Dylos DC1700 |
| Volatile Organic Compounds (VOCs) | Applied Sensor IAQ-engine |
| Humidity | Sensirion SHT15 |
| Temperature | Sensirion SHT15 |

It should be emphasized that all these sensors are factory calibrated with ensured measurement accuracy, repeatability and sensitivity. In addition, the measurement ranges of these sensors all meet the promulgated requirements of the national standards for IAQ monitoring.

Figure 4:
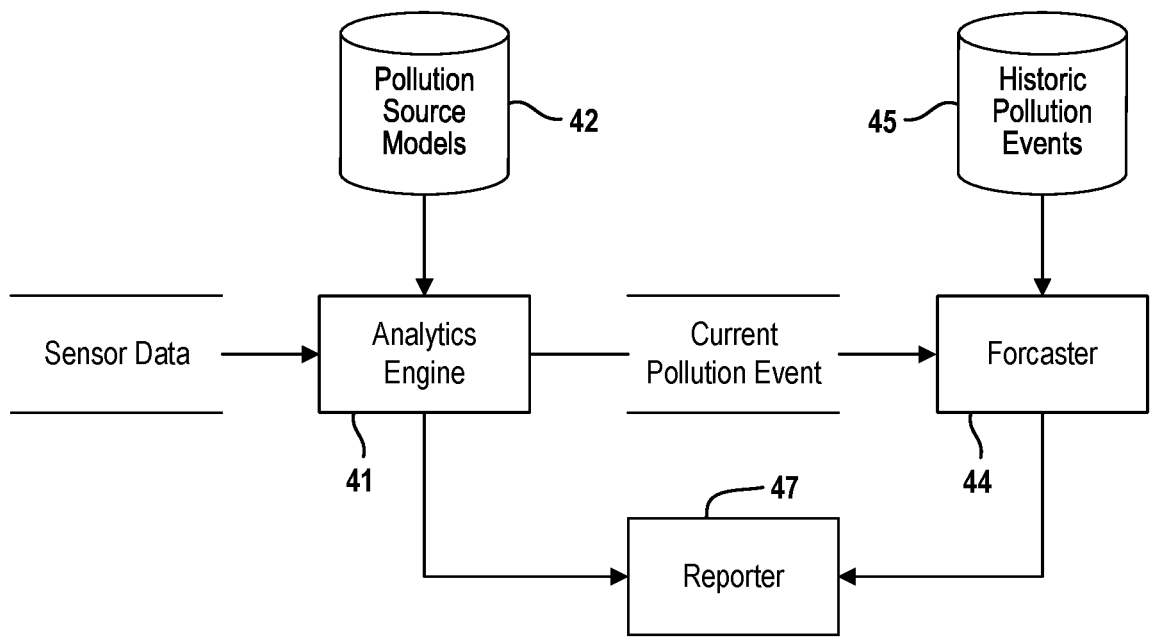
FIG. 4 is a block diagram of functional components of the air quality sensing and analytics system.

Logic components for the AirSense air quality sensing system 20 are further described in relation to FIG. 4. Given the streaming air quality sensor data, the analytics engine 41 detects the occurrence of the air pollution event. Indoor air pollution generated by the pollution events usually stays in the air for a very long time. People might have already inhaled a large amount of polluted air before the end of the events. To reduce the negative impact of indoor air pollution to health, it is critical to detect the occurrence of the pollution event as soon as possible.

Figure 5A:
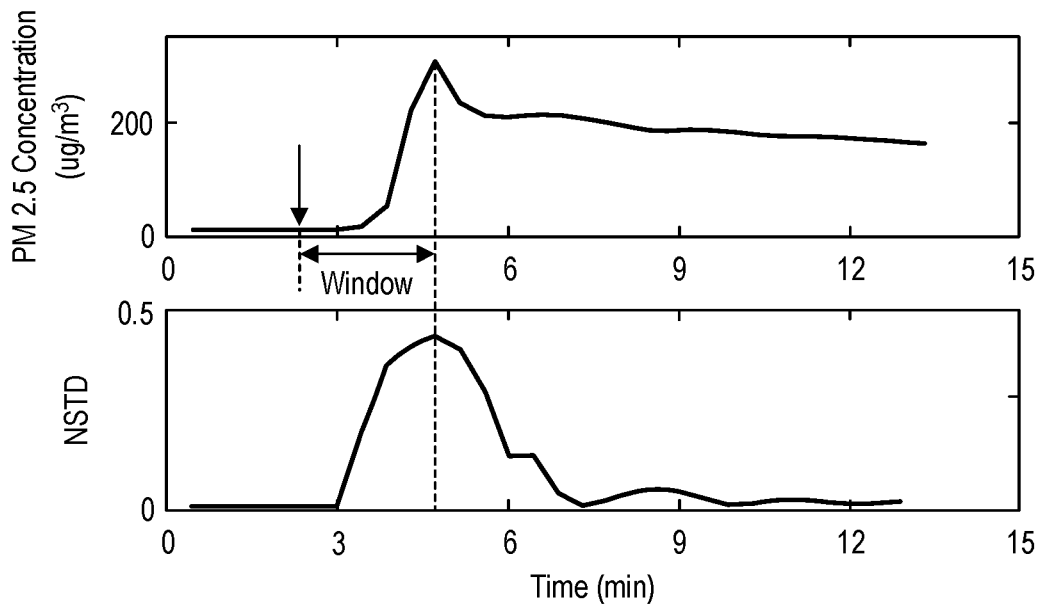
FIG. 5A are graphs illustrating the principle of the pollution event detection algorithm, where the upper plot shows the PM 2.5 sensor data of the pesticide spray pollution event and the lower plot shows the corresponding normalized standard deviation (NSTD) values.

Different techniques can be used to detect a pollution event from the sensor data. In one example embodiment, a normalized standard deviation (NSTD) based algorithm is used to detect the beginning of the air pollution event in real-time. As an illustration of this scheme, FIG. 5A presents an example of the PM 2.5 sensor data of a pesticide spray pollution event and its corresponding normalized standard deviation (NSTD) values. The key intuition behind the scheme is the observation that the beginning of an air pollution event is characterized by a sharp increase. To capture this sharp increase, a sliding window of size and a step size of one data point is used to segment the sensor data stream. The NSTD of the data points inside the window is computed. Specifically, let w be a window with $\beta$ data points $s_1, s_2, \ldots, s_\beta$. The NSTD of window w is calculated as $$NSTD(w) = \frac{1}{\max(w)} \sqrt{\frac{1}{\beta} \sum_{j=1}^{\beta} (s_j - \mu)^2} \quad (1)$$

where $\mu$ is the average of data points and $\max(w)$ is the maximum $s_j$ in window w. As shown in FIG. 5A, the NSTD value is low before the window reaches the sharp increase. As the window slides forward and gradually covers the sharp increase, the NSTD value increases until it reaches the maximum. As the window keeps sliding forward, the NSTD value decreases and goes back to a lower value. Given this observation, define the left end of the sliding window as the detection point of the pollution event when the right end of the sliding window reaches the maximum NSTD value.

In this example, there are two key parameters in the event detection algorithm. The first parameter is the window size.

Figure 5B:
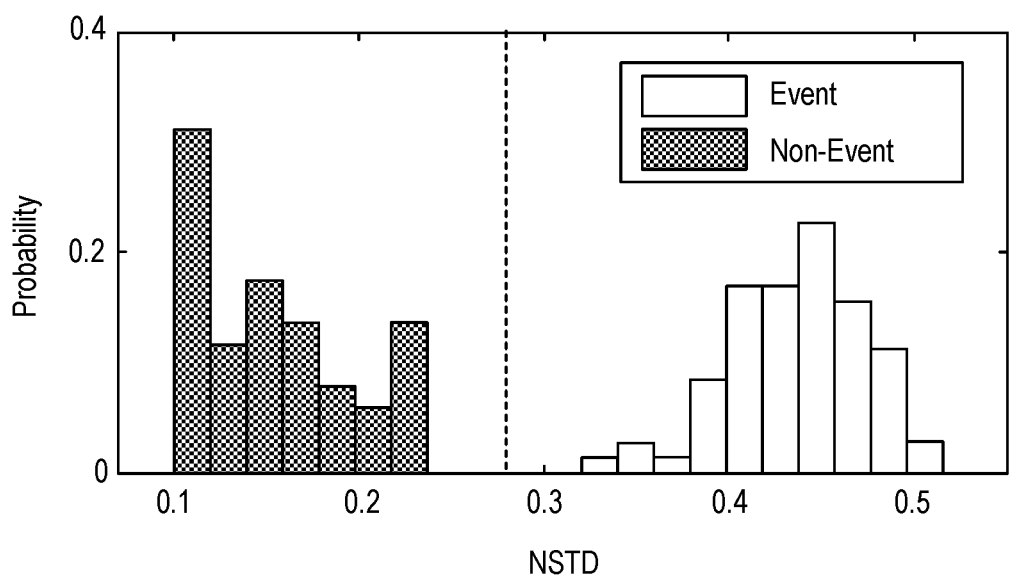
FIG. 5B is a bar graph showing a normalized histogram of maximum NSTD values of pollution events vs. non-pollution events.

A number of window sizes were empirically tested. It was found that equals to about three minutes works robustly across all the targeted pollution events although other window sizes are contemplated as well. This is because the air pollutants disperse very fast in the ambient atmosphere such that the peak of the concentrations of the air pollutants exhibits shortly after the occurrence of the air pollutants event. As such, this result indicates that the AirSense air quality sensing system 20 could detect the air pollution event within three minutes after the event occurs. The second parameter is the threshold of the maximum NSTD value Y which was used to determine whether there is a pollution event or not. Moreover, this threshold is also used to filter out non-pollution events including confounding events (e.g. vacuuming and walking on the carpet) and cases where nothing happens. FIG. 5B shows the normalized histogram of maximum NSTD values of the three pollution events and the non-pollution events. As illustrated, all the trials of the three pollution events have the maximum NSTD values larger than 0.3; whereas all the trials of non-pollution events have the maximum NSTD values less than 0.24. Based on this result, the threshold Y is set to be 0.27 in the example embodiment. Again, other threshold values also fall within the scope of this disclosure. Moreover, other signal processing techniques for detecting a spike or peak in the sensor data are also contemplated by this disclosure.

Because PM2.5 is one of the most common pollutants emitted during various pollution events, a particular matter sensor was chosen for the example embodiment. A volatile organic compound sensor, a humidity sensor, a temperature sensor as well as other types of sensors may also be used to detect pollution events assuming the events contain pollutants detectable by these sensors. With reference to FIGS. 1B and 1C, data from a humidity sensor and a volatile organic compound sensor, respectively, exhibit spikes for certain pollution event which may be detected using the NSTD approach described above. Thus, techniques for detecting pollution events can be extended to other sensor types. It should be noted that the threshold of NSTD over which the event is detected as pollution events would be recalibrated depending upon the pollutant and sensor type. It is also envisioned that input from multiple sensors working together will deliver a more reliable result.

After detecting the occurrence of the air pollution event, the second stage of the analytics engine is to identify the source for the pollution event. In the example embodiment, the pollution source identification problem is framed as a classification problem. As a first step, one needs to extract features that are able to discriminate different types of pollution events. As illustrated in FIG. 1, the key intuition behind feature extraction is the observation that air pollution sensor data within the window starting from the beginning of the pollution event to two minutes after the peak value contains enough information that captures the unique characteristics of the pollution events. This is also due to the fact that the air pollutants (i.e., PM 2.5 and VOCs) disperse very fast in the ambient atmosphere. In the meantime, although the humidity sensor data in the same window may not exhibit peak values, they contain distinctive patterns that, combined with the characteristics captured by the PM 2.5 and VOCs sensors, can be used to identify pollution sources.

Figure 6:
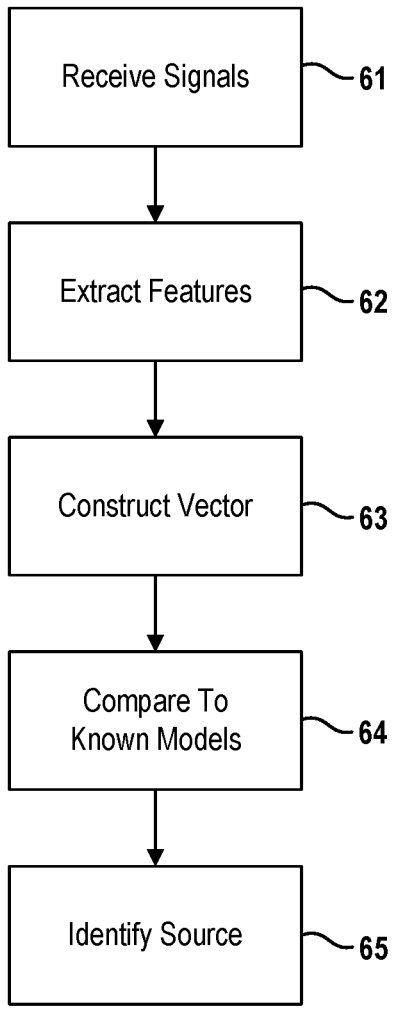
FIG. 6 is a flowchart depicting an example technique for identifying the source of a pollution event.

FIG. 6 depicts an example technique for identifying the source of a pollution event. Signals are received at 61 from one or more of the air quality sensors. From the signals, a pollution event may be detected, for example in the manner described above. Upon detecting a pollution event, steps are taken to identifying the source of the pollution event.

First, features are extracted at 62 from the sensor signals. In the example embodiment, a total of 18 features have been designed that capture the unique characteristics of the pollution events. These include single-sensor features extracted from PM 2.5, VOCs, and humidity sensor individually as well as cross-sensor features extracted from more than one sensor. Table 2 provides a listing of example features and their definitions.

TABLE 2

| | |
|---|---|
| Increase Rate | The increasing rate between the peak and the first data point of the window. |
| Increase Magnitude | The Difference between the peak and the first data point of the window |
| Decrease Rate | The decreasing rate between the peak and the last data point of the window |
| Decrease Magnitude | The difference between the peak and the last data point of the window |
| Standard Deviation | The standard deviation of all data points in the window |
| Change Magnitude | The difference between the maximum and minimum data points in the window |
| Standard Deviation | The standard deviation of all data points in the window |
| Change Magnitude Ratio | The change magnitude ratio among the three sensors |
| Standard Deviation Ratio | The standard deviation ratio among the three sensors |

Each feature is an element in a feature vector. These features are merely exemplary and other types of features also fall within the broader aspects of this disclosure.

Each of these features can be correlated to one or more of the source of pollution events. For example, the increase magnitude feature values of the PM2.5 sensor for smoking events are much higher than cooking and spraying pesticide because smoking events generate significant amounts of fine particles in a very short time. Similarly, the increase magnitude feature values of the humidity sensor for cooking events are much higher than smoking and spraying pesticide because cooking events generate significant amounts of vaporized waters that increase the humidity level of the indoor air. As another example, the decrease rate feature values of the VOCs sensor for spraying pesticide are much lower than smoking because pesticide sprays also contain vaporized water that can keep the VOCs stay in the air for a longer period of time. From these examples, it is readily understood how the extracted signal features can be correlated to the different sources of pollution. In this way, extracted signal features can be used to identify sources of pollution events.

In the example embodiment, features are extracted from a window of five minutes starting from the beginning of the air pollution event. A feature vector is constructed at 63 using the extracted features. The feature vector is imported into a trained classifier where the feature vector is compared to a plurality of predefined pollution source models. Essentially, the predefined models characterized each pollution source into one dedicated space in a high-dimensional feature space shared across all pollution sources. During inference, the feature vector of current pollution event is compared to the boundaries that separate pollution events in the feature space and then determined which pollution source it belongs to. In one example, a linear kernel-based Support Vector Machine is used as the classifier although other types of classifiers including discriminative classifiers, such as decision trees, generative classifiers, such as Gaussian Mixture Models and Hidden Markov Models, and non-parametric classifiers, such as K-nearest neighbor, can also be used.

Based on the comparison of the feature vector 64 to the models, the source of the pollution event can be identified as indicated at 65. More specifically, the source of pollution event is determined from the pollution source model that falls within a specified tolerance and most closely correlates to the feature vector. In the example embodiment, these steps are implemented by the analytics engine 41. It is understood that the pollution source models are stored in a non-transitory data store 42 as seen in FIG. 4. It is further understood that only the relevant steps of the methodology are discussed in relation to FIG. 6, but that other software-implemented instructions may be needed to control and manage the overall operation of the system.

It is worthwhile to note that the identification algorithm could identify pollution sources within five minutes after the occurrence of the pollution event. Considering the fact that it may take six to seven hours for the PM 2.5 and VOCs levels to drop below the unhealthy levels, the AirSense air quality sensing system 20 can notify people promptly about the identified pollution sources so that people can take actions to reduce the pollution at a much earlier time. For example, a reporter 47 interfaced with the analytics engine 141 is configured to present a notification for the pollution event on a display, where the notification includes the identified source of the pollution event.

After detecting a current pollution event, a forecaster 44 is configured to forecast the amount of pollution in the indoor setting at a future time based on the current pollution event as seen in FIG. 4. Based on the forecast, the AirSense air quality sensing system 20 can estimate the expected personal exposure to indoor air pollution and increase people's awareness of the potential harm of indoor air pollution. Different techniques for forecasting air quality can be employed by the AirSense air quality sensing system 20. For example, one straightforward scheme is to build a parametric regression model for each class of the air pollution events.

As a specific example, the air pollution level at a future time can be estimated by a simple parametric linear regression model in the form of $S_t=a_0+a_1*t$, where $S_t$ is the estimated air pollution level at a future time t; $a_1$ and $a_0$ are constant numbers. These two constant numbers can be determined based on collected training data. The simple parametric linear regression model can be generalized to a parametric polynomial regression model. Specifically, the air pollution level at a future time can be estimated by a parametric polynomial regression model in the form of $S_t=a_0+a_1*t+a_2*t^2++a_n t^n$, where $S_t$ is the estimated air pollution level at a future time t; $a_0, a_1, \ldots a_n$ are constant numbers. Again, the constant numbers can be determined based on collected training data. Other parametric models are also contemplated by this disclosure. Although parametric regression models can be used in this system, it is very challenging to build one parametric model that can make predictions reasonably well for all possible trials of the same class of the pollution events.

Figure 7:
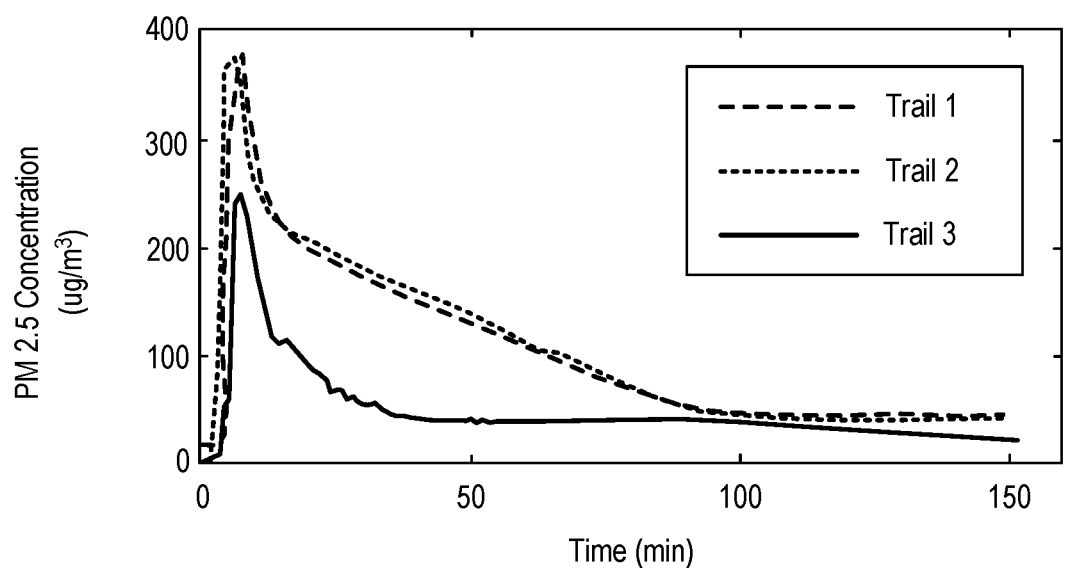
FIG. 7 is a graph showing an illustration of the principle of the IAQ forecast algorithm.

To resolve the issue of high within class variances, the AirSense air quality sensing system 20 adopts a non-parametric regression model to forecast the pollution caused by the air pollution event. The key intuition behind the non-parametric IAQ prediction algorithm is the observation that different trials of the same air pollution event have very similar shapes if their peak values are similar. As an example, FIG. 7 illustrates the PM 2.5 sensor data of three trials of the smoking event. As shown, trial 1 and 2 have similar peak values of about 380 ug/m³ and they exhibit very similar shapes. For trial 3, its peak value is about 250 ug/m³, and it has a very different shape compared to trial 1 and 2.

Figure 8:
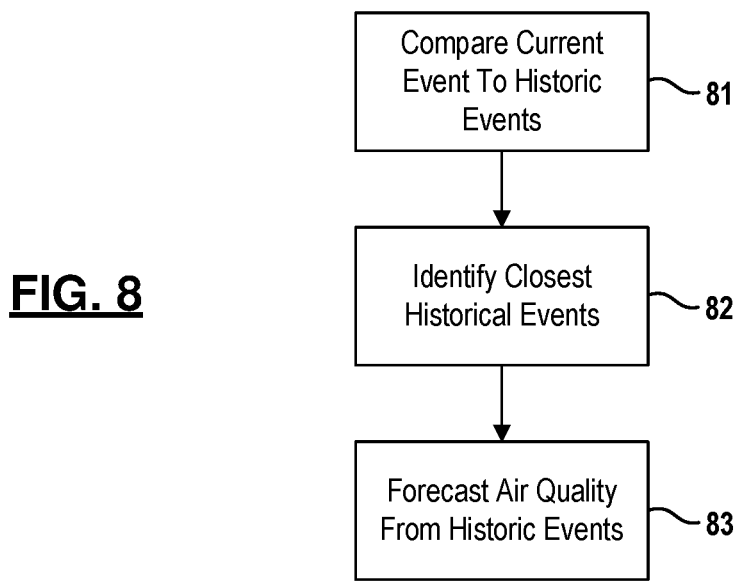
FIG. 8 is a flowchart depicting an example technique for forecasting air quality.

Based on the key intuition, an example technique for forecasting air quality is further described in relation to FIG. 8. First, a current pollution event is compared at 81 to a plurality of historic pollution events. Historic pollutions events describe the data captured during earlier pollution events. Such historic pollution events may include time series data from one or more sensors during an earlier pollution event.

From the comparison, the historic pollution events that most closely correlate to the current event are identified as indicated at 82. In an example embodiment, closely correlated means the historic events having the closest peak value to the current trial. More specifically, the non-parametric IAQ prediction algorithm first identifies q nearest historical trials of the same pollution event (e.g., q=3) whose peak values are within a threshold difference from the peak value of the current trial (e.g., n=10%). Other metrics may also be used to determine which historic events are closely correlated to the current pollution event.

Air quality can then be forecasted from the historic events that are closely correlated to the current pollution event as indicated at 83. In one embodiment, the air quality in the future is assumed to mimic the air quality from a single historic event which most closely correlates to the current event. That is, the concentration of pollutant at a given time (e.g., 20 minutes after the pollution event) is presumed to be the same as the concentration of the pollutant at that time during the historic event. In the example embodiment, these steps are implemented by the forecaster 44. It is understood that the historic pollution events are stored in a data store 45 as seen in FIG. 4. It is further understood that only the relevant steps of the methodology are discussed in relation to FIG. 8, but that other software-implemented instructions may be needed to control and manage the overall operation of the system.

In other embodiments, the air quality prediction is derived by the forecaster from two or more historic events which closely correlate to the current pollution event. For example, the squared error is calculated between the current trial and its q nearest historical trials respectively, with a sliding window of (e.g., n=10% in implementation) data points starting right after the peak value. Specifically, the current trial in the sliding window be $M_c=\{m_1, m_2, m_3, \ldots, m_n\}$, and the corresponding data points of the historical trial j be $M_{h_j}=\{m_{h_j}, 1, m_{h_j}, 2, m_{h_j}, 3 \ldots, m_{h_j}, n\}$, the squared error between these two trials is calculated as:

$$SE_j=\Sigma_{i=1}^n(m_i-m_{h_j,i}) \qquad (2)$$

A similarity metric, $s_j$, is based on the squared error and defined to measure the similarity between the current trial and the historical trial j among its q nearest historical trials:

$$s_j = \frac{1}{q-1}\left(1 - \frac{SE_j}{\sum_{i=1}^{q} SE_i}\right) \qquad (3)$$

where $s_j$ is normalized and $\Sigma_{i=1}^q sj=1$. The higher the sj, the more similarity between the current trial and the historical trial j. Based on the q nearest historical trials and their corresponding similarity metrics, one can predict the future air quality sensor values of the current trial for a prediction length l:

$$M_{predict} = \begin{bmatrix} S_1 \\ S_2 \\ \vdots \\ S_q \end{bmatrix}^T \begin{bmatrix} m_{h_1,n+1} & m_{h_1,n+2} & \cdots & m_{h_1,n+l} \\ m_{h_2,n+1} & m_{h_2,n+2} & \cdots & m_{h_2,n+l} \\ \vdots & \vdots & \ddots & \vdots \\ m_{h_q,n+1} & m_{h_q,n+2} & \cdots & m_{h_q,n+l} \end{bmatrix} \quad (4)$$

where $M_{predict} = \{m_{n+1}, m_{n+2}, m_{n+3}, \ldots, m_{n+l}\}$ is the predicted sensor values of the current trial and $\{m_{h_j,n+1}, m_{h_j,n+2}, m_{h_j,n+3}, \ldots, m_{h_j,n+l}\}$ is the sensor values of the historical trial j. In this way, sensor values for the current pollution event can be predicted at a time in the future from two or more historic events which closely correlate to the current pollution event. Other techniques for forecasting air quality from historic pollution events are also contemplated by this disclosure.

Figure 9:
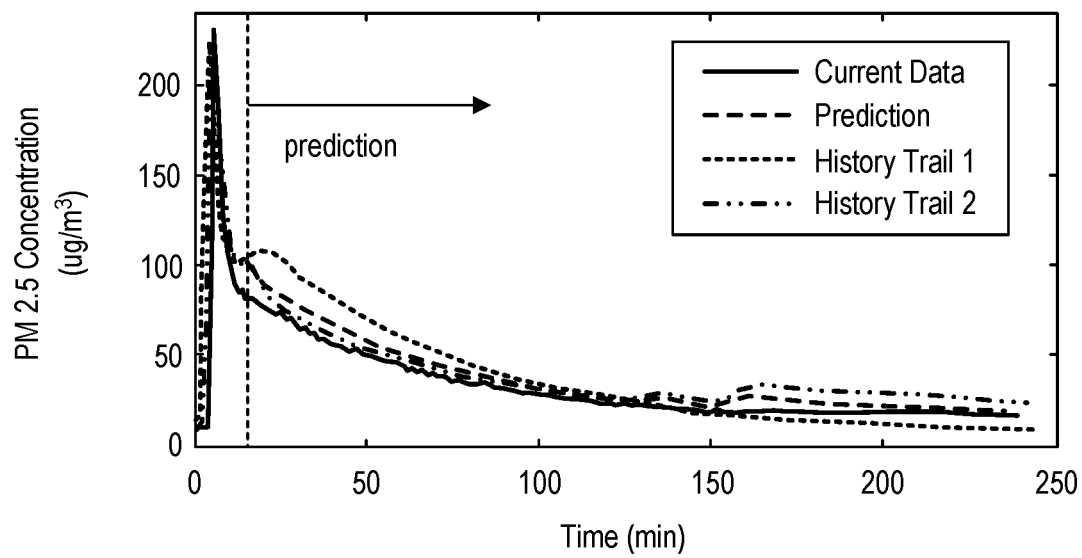
FIG. 9 is a graph showing an illustration of the proposed IAQ forecast algorithm in the context of predicting the PM 2.5 sensor values of a trial of pesticide spray event.

FIG. 9 illustrates an example of the performance of the IAQ prediction algorithm in the context of predicting PM 2.5 sensor values of a trial of pesticide spray event. The two dotted lines represent the two nearest historical trials of the current trial. The peak values of the two historical trials and the current trial are 224, 229 and 215 ug/m³, respectively. The prediction starts at the 11th data point after the peak value. As illustrated, the predicted sensor values match the real sensor data very well from the prediction starting point to 250 mins.

Another aspect of the AirSense air quality sensing system is to increase users' awareness of IAQ and assist users to take proper actions to cope with indoor air pollution in a timely manner. In the example embodiment, the application provides four different screens: (1) pollution event notification screen, (2) data visualization screen, (3) weekly IAQ report screen and (4) dashboard screen. These screens are further illustrated in FIGS. 10A-10D.

FIG. 10A depicts a pollution event and source notification screen. Once an indoor air pollution event is detected and its source is identified, the analytics engine on the cloud server immediately sends a notification to the mobile application, which provides a link to a pollution event screen (FIG. 10A). The pollution event screen lists the air pollution sources identified by the AirSense system, and the estimated duration until the air quality will return back to healthy level, based on the result of the IAQ forecast algorithm. This is based on the previous observation that proper use of simulations are known to be effective in persuading people to change their attitudes or behaviors by enabling them to observe immediately the link between cause (e.g., no action) and effect (e.g., exposure to pollution for 30 minutes). Finally, detailed pollution source-specific suggestions are provided to encourage a user to take actions to cope with indoor air pollution event. The suggestions are adopted from the authoritative guidance provided by EPA (US Environmental Protection Agency). Table 3 lists example pollution sources and corresponding suggestions.

TABLE 3

| Pollution Source | Suggestions |
| --- | --- |
| Cook | Please turn on the range hood when cooking and ventilate your home. |
| Smoke | Please smoke outside to minimize indoor pollution and ventilate your home. |
| Spray Pesticide | Please ventilate your home after spraying pesticide. |

FIG. 10B depicts a data visualization screen. The data visualization screen provides a detailed visualization of the air quality sensor history and statistics (max, min and average) in the past 24 hours, as well as IAQ prediction data provided by AirSense system. By zooming in and out on the visualization, users can examine the sensor data in details at any time within the past 24 hours. Furthermore, to draw users' attention when the air quality degrades, we map the sensor data to the official air quality index (AQI) from EPA based on a standard lookup table The same color codes of AQI to visualize the sensor data in different colors are used. At the bottom of the page, a web link on the background knowledge of the air pollutant from EPA is provided for further details.

Figure 10C:
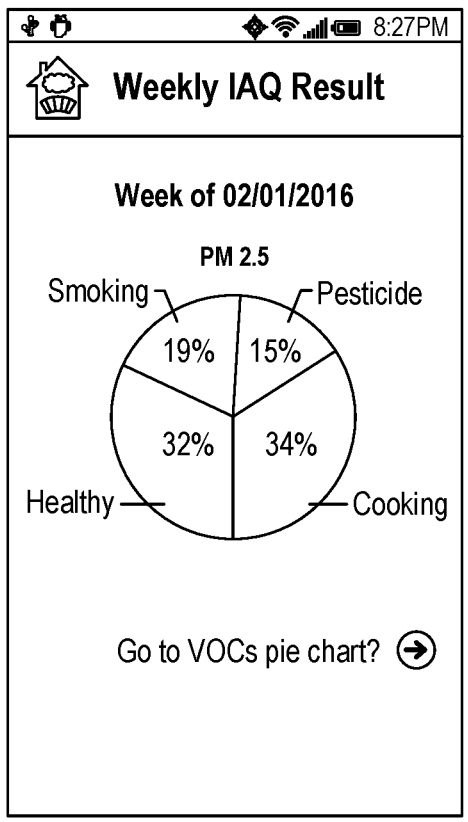

FIG. 10C depicts a weekly IAQ report screen. The analytics engine generates a weekly IAQ report which summarizes the amount of indoor air pollution caused by pollution events every week. This screen is designed for self-monitoring, which is known to be beneficial for people in understanding how well they are performing the target behavior, increasing the likelihood that they will continue to produce the behavior. The weekly IAQ report is illustrated using a pie chart, which shows the percentage of time during one week for IAQ being either healthy or polluted by the three pollution source categories. The AQI standard was followed from EPA to group the AQI categories of good and moderate as healthy and group the other four AQI categories as unhealthy. FIG. 10C shows a sample weekly IAQ report, illustrating that the PM 2.5 is at healthy level for 32% of the week while the PM 2.5 is at unhealthy level for 19%, 15%, and 34% of the week due to smoking, spraying pesticide, and cooking, respectively.

Figure 10D:
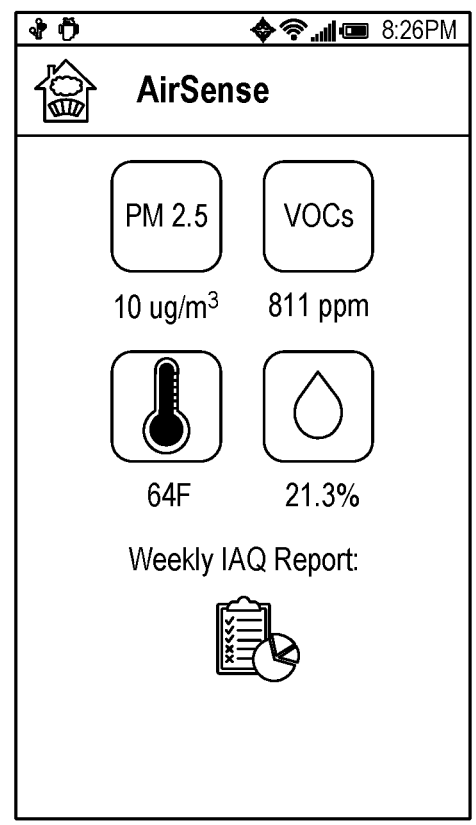

FIG. 10D depicts a dashboard screen. A dashboard screen is accessible by executing the application manually. It has four icons each representing one air quality sensor included in AirSense with real-time measurements shown below. On the home page, there are four icons each representing one air quality sensor included in AirSense. The number below each icon is the real-time measurement from each sensor. By pressing each icon, the data visualization page will be displayed. At the bottom, users can check their weekly IAQ reports by pressing the weekly IAQ report icon.

AirSense air quality sensing system proposed herein was evaluated by conducting extensive experiments to examine the performance of the system on pollution event detection, pollution source identification and IAQ forecast under different experimental conditions.

In the experimental setup, two families volunteered to help collect data and conduct evaluation experiments at their places of residence. Family 1 has three members: 1) $P_{11}$ is a 32-year-old male university researcher; 2) $P_{12}$ is a 31-year-old female university researcher; and 3) $P_{13}$ is a 59-year-old retired female. Family 2 only consists of one member, $P_{21}$, a 25-year-old male university student.

AirSense air quality sensing system was deployed in the living room at each home. The approximate size of the living room of two homes is 56 m² and 25 m², respectively. The living room was chosen as the deployment site of the AirSense air quality sensing system because it is the central place that is close to kitchen, bedrooms, restrooms as well as windows for ventilation.

AirSense air quality sensing system was deployed at each home for a duration of ten weeks. To collect IAQ data, two families were instructed to regularly cook in the kitchen as well as smoke and spray pesticide in the living room. It should be emphasized that the occupants were allowed to conduct multiple pollution activities simultaneously (e.g., $P_{11}$ is smoking while $P_{12}$ is cooking). Therefore, there are in total seven types of pollution events (individuals plus combinations). Table 4 below lists these seven types of pollution events and their abbreviations.

TABLE 4

| Event | Cook | Smoke | Spray | Cook + Smoke | Smoke + Spray | Cook + Spray | All |
|---|---|---|---|---|---|---|---|
| Abbreviation | C | S | P | CS | SP | CP | CSP |

For the ground truth collection, the occupants were asked to label the pollution events and record the timestamps of the events using Google Sheets. The time periods other than the pollution events during the ten week duration are categorized as non-pollution/null events. Table 5 lists the number of pollution events and their corresponding time durations collected during the ten week deployment.

TABLE 5

|  | Activity | C | S | P | CS | SP | CP | CSP | Total |
|---|---|---|---|---|---|---|---|---|---|
| Family 1 | No. of Sample | 23 | 22 | 24 | 18 | 18 | 19 | 15 | 139 |
|  | Duration (h) | 140 | 112 | 101 | 84 | 89 | 93 | 69 | 688 |
| Family 2 | No. of Sample | 25 | 25 | 25 | 20 | 20 | 20 | 15 | 150 |
|  | Duration (h) | 180 | 146 | 164 | 112 | 122 | 108 | 78 | 910 |

Table 6 presents the confusion matrices for detecting the pollution events at two families. Observe that the pollution event detection rates at both houses are extremely high, which demonstrates the algorithm is very accurate at detecting pollution events regardless of the differences in floor plans of the homes as well as living styles of occupants at two families. In addition, it was also observed that the false positive rates at both families are extremely low. The results indicate the algorithm is very robust to noises caused by environmental changes and other human behaviors.

TABLE 6

|  | Actual/Predicted | Event | Null |
|---|---|---|---|
| Family 1 | Event | 99.8% | 0.2% |
|  | Null | 1.1% | 98.9% |
| Family 2 | Event | 100.0% | 0.0% |
|  | Null | 0.5% | 99.5% |

The performance of the pollution source identification scheme using leave-one-trail-out cross validation strategy was evaluated. Table 7 and Table 8 show the confusion matrices for the source identification of pollution events at two families, respectively. Each row denotes the actual pollution event conducted and each column represents the pollution event identified by AirSense air quality sensing system. Overall, the average pollution event identification accuracy is 94.2% for Family 1 and 97.3% for Family 2. This result demonstrates that the system can accurately identify sources of the pollution events across different families because of the highly discriminative features that were carefully designed. When taking a closer look at the identification accuracies of different events, it was observed that the pollution events that involve more than one pollution sources have relatively lower identification accuracies than pollution events that involve only one pollution source. This is because when multiple pollution sources exhibit at the same time; the air pollutants generated by different sources are mixed together, making the source identification problem more challenging.

TABLE 7

|  | C | S | P | CS | SP | CP | CSP | Recall (%) |
|---|---|---|---|---|---|---|---|---|
| C | 23 | 0 | 0 | 0 | 0 | 0 | 0 | 100.0 |
| S | 0 | 22 | 0 | 0 | 0 | 0 | 0 | 100.0 |
| P | 0 | 0 | 24 | 0 | 0 | 0 | 0 | 100.0 |
| CS | 0 | 1 | 0 | 17 | 0 | 0 | 0 | 94.1 |
| SP | 2 | 0 | 0 | 0 | 16 | 0 | 0 | 88.9 |
| CP | 0 | 1 | 0 | 1 | 0 | 17 | 0 | 89.5 |
| CSP | 0 | 1 | 0 | 1 | 0 | 1 | 12 | 80.0 |
| Precision (%) | 92.0 | 88.0 | 100.0 | 89.5 | 100.0 | 94.4 | 100.0 |  |

TABLE 8

|  | C | S | P | CS | SP | CP | CSP | Recall (%) |
|---|---|---|---|---|---|---|---|---|
| C | 25 | 0 | 0 | 0 | 0 | 0 | 0 | 100.0 |
| S | 0 | 25 | 0 | 0 | 0 | 0 | 0 | 100.0 |
| P | 0 | 0 | 25 | 0 | 0 | 0 | 0 | 100.0 |
| CS | 0 | 0 | 0 | 20 | 0 | 0 | 0 | 100.0 |
| SP | 0 | 0 | 1 | 0 | 19 | 0 | 0 | 95.0 |
| CP | 1 | 0 | 0 | 0 | 0 | 19 | 0 | 95.0 |
| CSP | 0 | 0 | 0 | 0 | 1 | 1 | 13 | 86.7 |
| Precision (%) | 96.1 | 100.0 | 96.1 | 100.0 | 95.0 | 95.0 | 100.0 |  |

The normalized root mean square deviation (NRMSD) was used as the evaluation metric to examine the performance of the IAQ forecast scheme. Formally, NRMSD is defined as $$NRMSD = \frac{\sqrt{\frac{1}{l}\left(\sum_{i=1}^{l}(\hat{m}_i - m_i)^2\right)}}{\hat{m}_{max} - \hat{m}_{min}} \quad (5)$$

where $\hat{m}_i$ and $m_i$ are the observed value and predicted value respectively, l is the prediction length, and $\hat{m}_{max}$ and $m_{min}$ are the maximum and minimum of the observed values over the prediction length l. NRMSD is often expressed as a percentage, where lower values indicate better performance.

The IAQ forecast algorithm was evaluated on every trial of the pollution events based on leave-one-trial-out cross validation strategy. For each trial, set the ending point of the prediction at the point where the air quality data reaches the healthy level provided by the EPA standard. The prediction starting point is defined as the time duration after PM 2.5 or VOCs reaches the peak value. The prediction length l is the distance between the ending point and the starting point.

Figure 11:
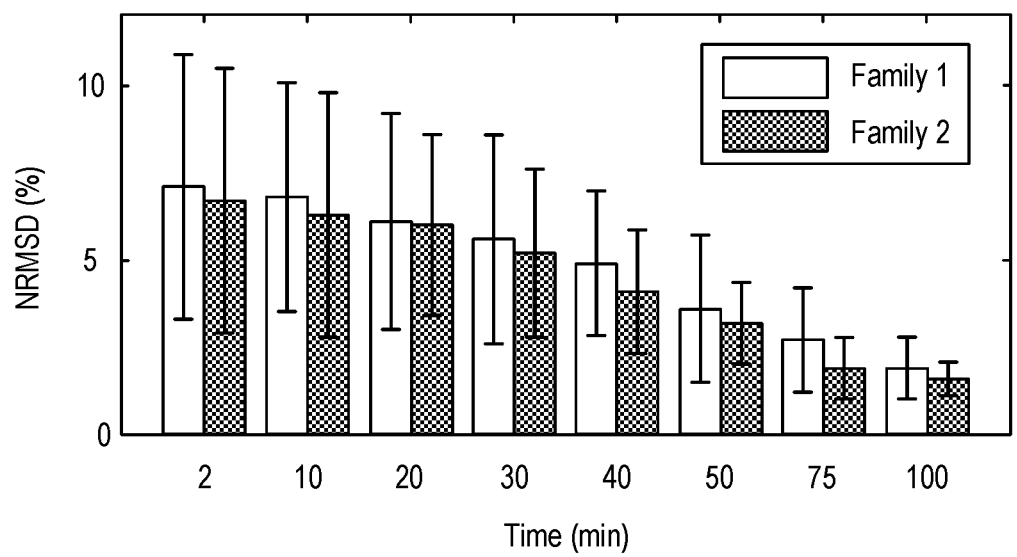
FIG. 11 is a graph showing performance of the IAQ forecast algorithm on PM 2.5 prediction for two families.
Figure 12:
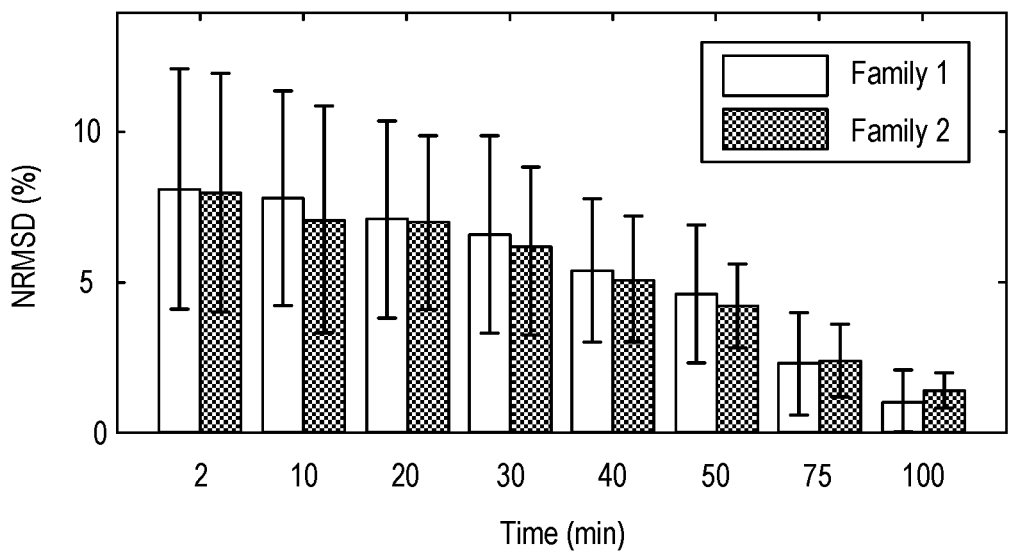
FIG. 12 is a graph showing performance of the IAQ forecast algorithm on VOC's prediction for two families.

FIG. 11 illustrates the performance of the IAQ forecast algorithm on PM 2.5 prediction across seven pollution events at two families. The horizontal axis represents the prediction starting point. The vertical axis represents the NRMSD value calculated over the prediction length. As illustrated, the NRMSD values decrease as the prediction starting point moves forward. This result indicates that IAQ information can be forecasted more accurately when time elapses. Moreover, it was observed that the IAQ forecast algorithm performs very well even if start predicting the future PM 2.5 sensor values at two minutes after the peak value, achieving an average NRMSD of 6.8% for Family 1 and 6.5% for Family 2. This forecast is accurate enough to capture the trend and severity of the PM2.5 pollution. Similar results are observed in FIG. 12 for forecasting the VOCs sensor values. In all, the results demonstrate that the IAQ forecast algorithm can provide a reasonably accurate prediction on future IAQ within a very short time after the occurrences of the pollution events.

Figure 15:
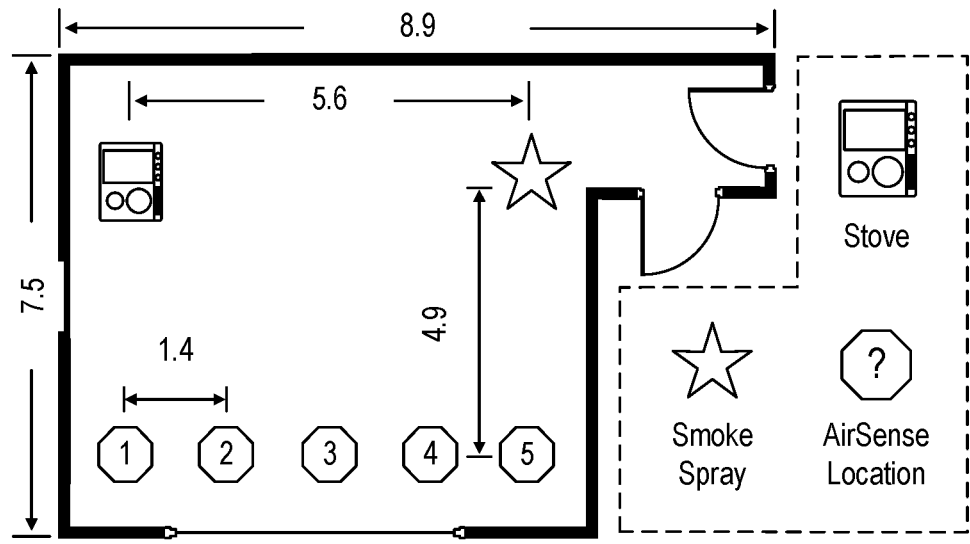
FIG. 15 is a diagram showing the illustration of the floor plan of the living room and the deployment locations of the air quality sensing system.

In this experiment, the impact of the deployment location of AirSense air quality sensing system was also evaluated on the performance of the system. Specifically, the pollution event detection latency as well as the source identification accuracy were examined when deploying AirSense air quality sensing system at different room locations. To evaluate the impact, the experiment was conducted in the living room at Family 1. FIG. 15 depicts the floor plan of the room and the deployment locations of AirSense in the experiment. As shown, AirSense air quality sensing system was deployed at five different locations with 1.4 meters apart. The occupants in Family 1 were instructed to cook at the stove as well as smoke and spray pesticide at the location marked as a star. Each of the seven pollution events listed in Table 4 was conducted ten times while AirSense air quality sensing system was placed at each deployment location.

Figure 13:
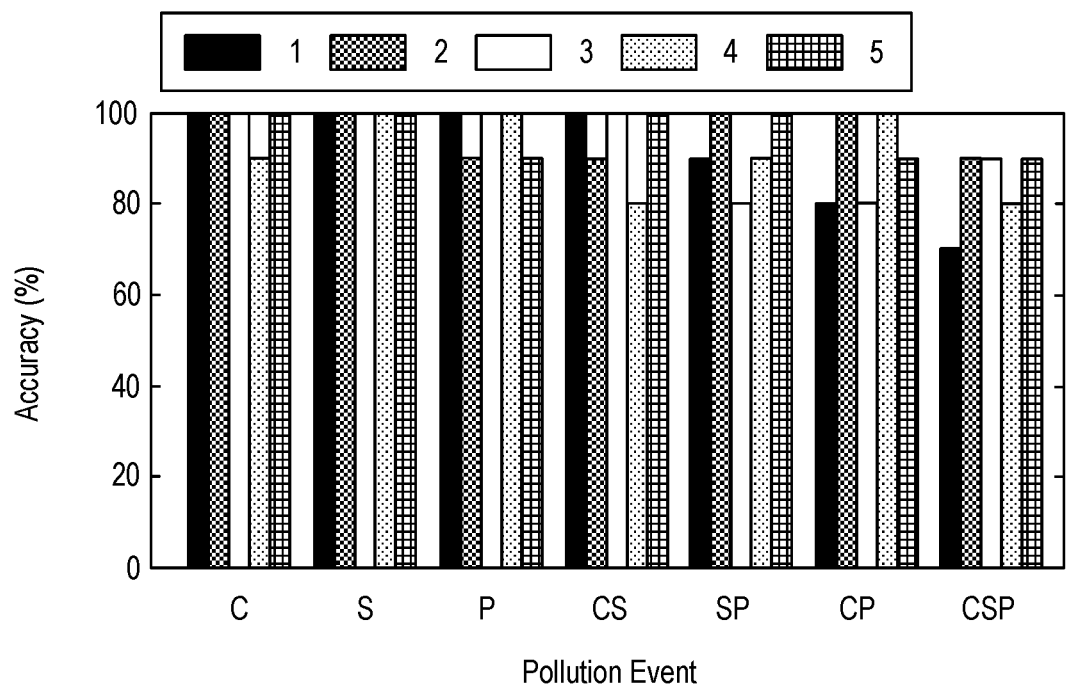
FIG. 13 is a graph showing pollution source identification accuracy at five deployment locations.
Figure 14:
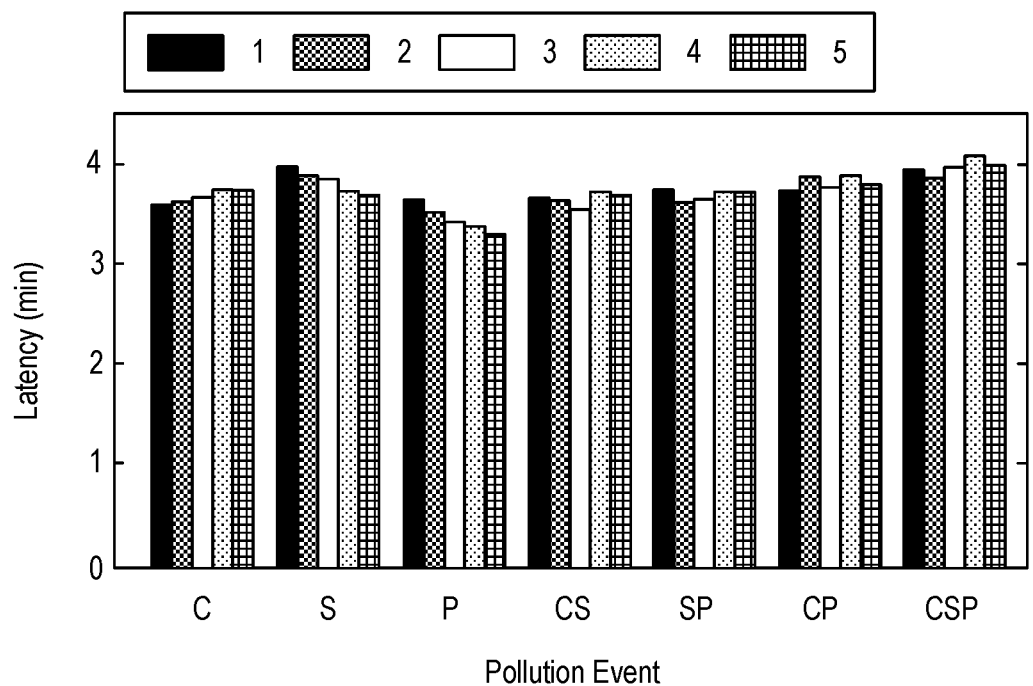
FIG. 14 is a graph showing pollution source identification latency at five deployment locations within an indoor setting.

FIG. 13 presents the average pollution source identification accuracies across ten trials at five deployment locations. It was observed that although the accuracies at different deployment locations vary, the differences among the five deployment locations are not significant. FIG. 14 presents the average pollution source identification latencies across ten trials at five deployment locations. The latency is defined as the duration between the occurrence of the pollution event and the time when the pollution source is identified. It was observed that the largest latency across all five deployment locations is 4.1 mins. This result indicates that even if the living room is large (56 m$^2$), AirSense is able to detect the pollution event and identify the source in a timely manner. Moreover, it was observed that although the latencies at different deployment locations vary, the differences among the five deployment locations are not significant. In all, the results indicate that the impact of variation of deployment location on the accuracy and latency of pollution source identification is minor.

Finally, the impact we evaluate the impact of the diversity of pollution sources was evaluated on the performance of AirSense. Specifically, the source identification accuracy on different cooking styles, different numbers of cigarettes being smoked and different brands of pesticide was examined. Table 9 summarizes the subcategories within each pollution source. To evaluate the impact, the occupant in Family 2 was instructed to perform ten trials for each pollution activity for all the subcategories. These trials were used as the test set and test them using the source identification models we built from the data summarized in Table 5. As shown in Table 9, AirSense air quality sensing system is able to accurately identify pollution sources across diverse subcategories.

TABLE 9

| Source | Subcategory | Accuracy |
|---|---|---|
| Cook | Grill | 100.0% |
|  | Barbecue | 90.0% |
|  | Fry | 100.0% |
|  | Steam | 100.0% |
|  | Stew | 80.0% |
| Smoke | 2 Cigarettes SI | 100.0% |
|  | 2 Cigarettes CO | 100.0% |
|  | 3 Cigarettes SI | 90.0% |
|  | 3 Cigarettes CO | 100.0% |
|  | 2(SI) + 1 (CO) Cigarettes | 100.0% |
| Spray | Pesticide brand one | 100.0% |
|  | Pesticide brand two | 100.0% |
|  | Pesticide brand three | 90.0% |

As the second part of the evaluation, a real-world deployment study was conducted to 1) evaluate the system performance of AirSense in uncontrolled, daily life settings and 2) examine the potential of AirSense in increasing users' awareness of IAQ and promoting behavioral changes to improve IAQ.

Three additional three families volunteered to contribute. Family 3 has two members: 1) $P_{31}$ is a 56-year-old housewife and 2) $P_{32}$ is a 58-year-old male engineer. Family 4 also has two members: 1) $P_{41}$ is a 29-year-old female university researcher and 2) $P_{42}$ is a 30-year-old male university researcher. Family 5 has one member: $P_{51}$ is a 23-year-old male university student. A survey before recruit was made to make sure the three families met the criteria: 1) at least one member of each family was a smoker; 2) they have habits of spraying pesticide; and 3) they cook frequently.

The real-world deployment study consists of two phases. In phase one, AirSense without the smartphone application was deployed to continuously collect the IAQ data at three families in their living rooms (size: 31, 44 and 19 m$^2$, respectively) for six weeks. Note that the screens of AirSense were turned off so that users had no access to the data. The occupants at three families were asked to log the ground truth of the pollution events using Google Sheets. The collected IAQ data and the ground truth were used to build the models for pollution event detection, pollution source identification as well as IAQ forecast. In phase two, the smartphone app was installed on the participants' smartphones and AirSense was deployed at the same three families for another three weeks. The occupants could use the app to check IAQ information and get notifications about the detected pollution events, identified pollution sources, IAQ forecast and the suggestions. In this phase, the occupants were encouraged to think aloud and take a memo. Table 10 lists the number of pollution events and their corresponding time durations collected from the three families.

TABLE 10

| Activities | | C | S | P | CS | SP | CP | CSP | Total |
|---|---|---|---|---|---|---|---|---|---|
| Family 3 | No. of Sample | 80 | 23 | 12 | 3 | 4 | 1 | 0 | 123 |
|  | Duration (h) | 480 | 128 | 70 | 19 | 23 | 6 | 0 | 726 |
| Family 4 | No. of Sample | 120 | 17 | 25 | 4 | 4 | 1 | 0 | 171 |
|  | Duration (h) | 710 | 80 | 140 | 21 | 29 | 6 | 0 | 986 |
| Family 5 | No. of Sample | 28 | 53 | 16 | 3 | 0 | 3 | 0 | 103 |
|  | Duration (h) | 150 | 270 | 93 | 19 | 0 | 15 | 0 | 547 |

To evaluate the potential of AirSense, a semi-structured interview was conducted at the end of phase two. During the interview, the occupants were asked about their overall usage experiences of AirSense, including their behavioral changes related to their IAQ. All think-aloud and interview data were transcribed and analyzed using open coding to examine emerging themes. An affinity diagram was created for axial coding to understand common themes and patterns across the codes that were generated.

Figure 16:
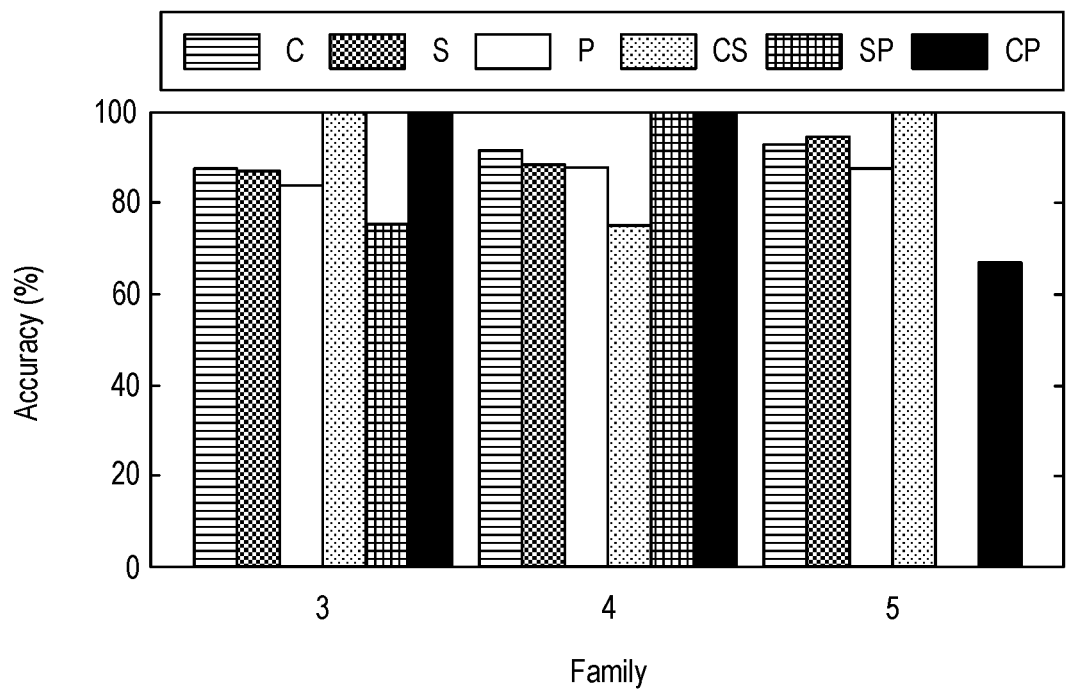
FIG. 16 is a graph showing pollution source identification accuracy in daily life settings. Note that there was no S+P event performed from Family 5.

The system performance of AirSense in daily life settings was evaluated at the three families. In terms of pollution event detection, the average true positive and true negative rates across the three families are 99.0% and 99.5%. In terms of pollution source identification, as illustrated in FIG. 16, the average source identification accuracies of 87.0%, 90.7% and 92.2% were achieved across all pollution events at three families. It should be noted that there was no CSP event performed by all three families during the deployment. Additionally, there was no SP event performed by Family 5. In terms of IAQ forecast, the average NRMSD when starting prediction at two minutes after the peak value is 7.3% for Family 3, 7.9% for Family 4, and 7.5% for Family 5.

Figure 17:
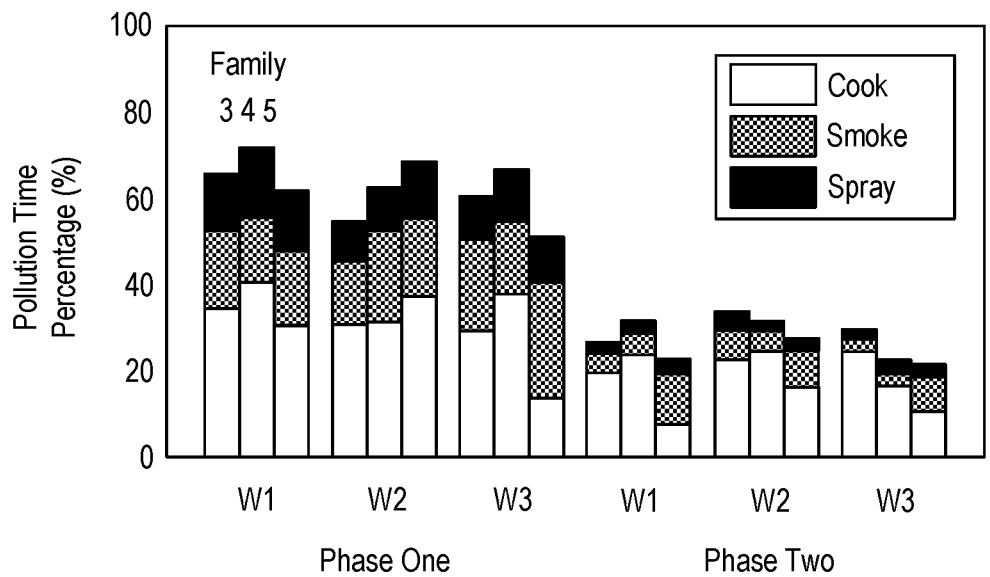
FIG. 17 is a graph showing the weekly PM 2.5 profiling of indoor air pollution for three families.
Figure 18:
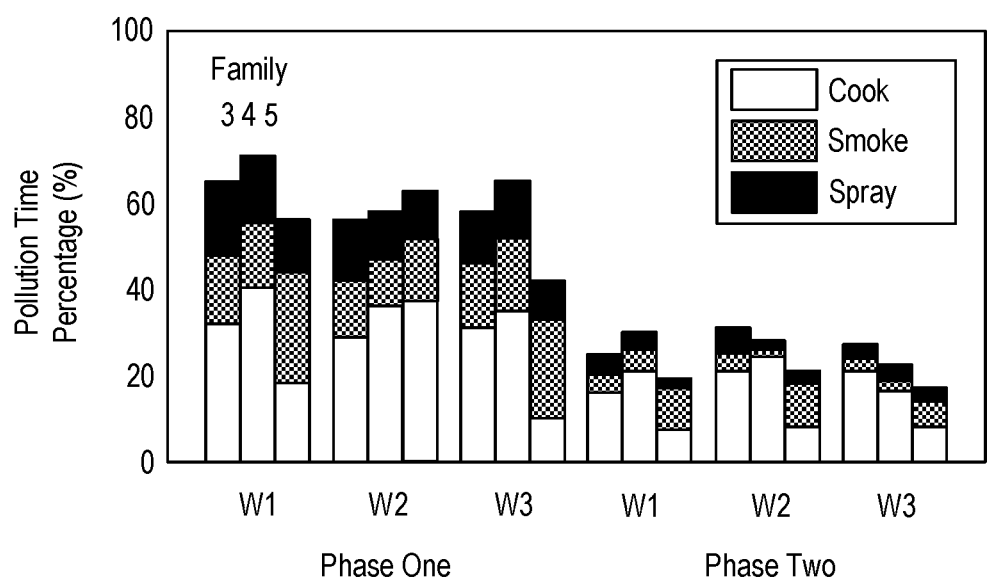
FIG. 18 is a graph showing the weekly VOCs profiling of indoor air pollution for three families.

FIG. 17 and FIG. 18 present the weekly profiling of indoor air pollution caused by cooking, smoking and spraying pesticide at three families in terms of PM 2.5 and VOCs, respectively. In order to make a clear comparison between the two phases of our real-world deployment study, we put the 3-week profiling of phase one (last 3 weeks of total six weeks) and the 3-week profiling of phase two into the same figure, with phase one on the left and phase two on the right. The three-stack bars represent the time percentage of indoor air polluted by one of the three pollution activities, with the remaining percentage representing time of having healthy air. As shown in both figures, the pollution time percentage of phase one is much higher than that of phase two. This result demonstrates the significant potential of AirSense in leading to better IAQ.

Participants first talked about how much they were unaware of indoor air quality or pollution sources before trying AirSense. They were able to notice the air quality was not good without the system, but did not have concrete idea how bad the air quality was: "Sometimes, I don't feel very well, and I guess it's related to the air quality at home, but I don't know exactly (it was)." ($P_{41}$); "It feels good to see actual numbers [ . . . ] rather than just guessing (the quality)." ($P_{32}$) This finding agrees with prior studies in that lack of detailed information can lead to lower level of awareness or even overlooking.

Visual and quantified representations of air quality were recognized as contributing factors toward increased awareness of the participants, which is consistent to the prior study of IAQ visualizer: "The graphs with waves of numbers are pretty intuitive. [ . . . ] (it was) good to see the actual numbers that can tell me how good air quality is at my home." ($P_{32}$)

Participants noted that they were curious about which pollution source leads to specific subjective feeling or sense: "I often asked myself what were the reasons for the changes" ($P_{32}$). Detailed information of pollution source provided by AirSense helped them in mapping specific feeling or sense with corresponding air pollution source: "When I was browsing those data. I really enjoyed thinking about which aspect of air quality might be related to my bad feeling. [ . . . ] it gave me lots of useful hints." ($P_{41}$)

The participants shared opinions about the role of AirSense as a trigger for their actions toward better IAQ. $P_{51}$ talked that the timely notification of AirSense reminded him to cope with bad air quality condition which can be easily overlooked; "When I was cooking steak, the air quality plumped greatly and AirSense gave me a warning and asked me to turn on the range hood." Also, pollution notifications motivated users to follow the suggestions of AirSense; "Whenever I saw the red dots that tell me something was not good. I always checked the suggestions on the mobile app." ($P_{42}$)

For IAQ control, participants also talked about their increased competence, which is one key factor of intrinsic motivation from the viewpoint of Self-Determination Theory, due to accurate and timely feedback of IAQ changes from AirSense. The system actually helped them have air quality in control: "it told me to open the window, which really helped to bring the numbers back to the normal range." ($P_{42}$); "when I cooked, AirSense can detect my cooking activities and I found that range hood really helped to lower down both gas and particle pollutants. ($P_{31}$) Also, once they realize their action can make meaningful changes of IAQ, they became more engaged in the active behavior for IAQ control: "But since I found it's useful to bring me better air I wouldn't mind doing it, and it's becoming something that is on the top of my head now." ($P_{42}$).

The evaluation results indicate AirSense is a very promising home-based ubiquitous computing technology for IAQ analytics. AirSense bridges the gap of existing IAQ monitoring systems by leveraging machine learning-based algorithms to identify pollution sources of the detected pollution events as well as forecast future IAQ changes to estimate the personal exposure to indoor air pollution. Extensive experiments in both controlled and daily life settings have been conducted to evaluate the performance of AirSense. The results show that AirSense can identify cooking, smoking, spraying pesticide pollution events and their combinations, which are among the most common household activities that generate significant indoor air pollution. AirSense can also forecast future air quality sensor values with a high accuracy. Finally, our deployment study shows the potential of AirSense in increasing users' awareness of IAQ and helping reduce air pollution at homes.

In some embodiments, the techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various computing devices may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for identifying source of a pollution event in an indoor setting, comprising:
   measuring, by a sensor, concentration of particulates in air of the indoor setting;
   applying, by a signal processor, a sliding time window to a signal from the sensor, where the duration of the sliding time window is less than the duration of the signal;
   for each time interval captured by the sliding time window, computing, by the signal processor, a normalized standard deviation for values in the sliding time window;
   determining, by the signal processor, a maximum value for the normalized standard deviation across the time intervals;
   correlating, by the signal processor, time at which the maximum value occurs to a pollution event in the indoor setting;
   extracting, by the signal processor, features proximate to the pollution event, where the features are extracted from the signal in response to detecting the pollution event;
   constructing, by the signal processor, a feature vector using the extracted features;
   comparing, by the signal processor, the feature vector to a plurality of pollution source models, where each pollution source model represents a different pollution event and a source for the pollution event;
   identifying, by the signal processor, a source of the pollution event based on the comparison of the feature vector with the plurality of pollution source models.

2. The method of claim 1 wherein the features are extracted within a window of time, such that the window of time is centered about the peak in the signal.

3. The method of claim 1 wherein the features are selected from a group consisting of increasing rate between the peak and a first data point in the window of time, a difference between the peak and the first data point in the window of time, a decreasing rate between the peak and a last data point in the window of time, a difference between the peak and the last data point in the window of time, and a standard deviation of all data points in the window of time.

4. The method of claim 1 wherein each pollution source model in the plurality of pollution source models is defined as a Support Vector Machine.

5. The method of claim 1 wherein source of the pollution event is selected from a group consisting of cooking, smoking and spraying pesticide.

6. The method of claim 1 further comprises
   receiving a second signal from at least one of a humidity sensor or a volatile organic compound sensor; and
   extracting features proximate to the pollution event from the second signal in response to detecting the pollution event.

7. The method of claim 1 further comprises notifying a person of the pollution event in response to detecting the pollution event, where the notification includes the identified source of the pollution event.

8. The method of claim 1 further comprises forecasting amount of pollution in the indoor setting at a future time, where the forecasting is in response to detecting the pollution event.

9. The method of claim 8 further comprises forecasting amount of pollution using a parametric model.

10. The method of claim 8 wherein forecasting amount of pollution includes comparing the pollution event to a plurality of historic pollution events, identify a given historic pollution event from the plurality of historic pollution events that correlates to the pollution event and determining an amount of pollution at the future time using the given historic pollution event.

11. The method of claim 1 further comprises measuring pollutants using a sensor disposed in the indoor setting, wherein the sensor is at least one of a particulate matter sensor, a volatile organic compound sensor and a humidity sensor.

12. A system for sensing air quality in an indoor setting, comprising:

a particulate matter sensor configured to measure concentration of particulates in the indoor setting;

a data store for storing a plurality of pollution source models, where each pollution source model in the data store represents a different pollution event and identifies a source for the pollution event;

an analytics engine configured to receive a signal from the particulate matter sensor and interfaced with the data store, the analytics engine detects a pollution event from the signal, extracts features from the signal in response to detecting the pollution event, and constructs a feature vector using the extracted features, wherein the analytics engine compares the feature vector to the plurality of pollution source models in the data store and identifies a source of the pollution event based on the comparison of the feature vector with the plurality of pollution source models, where the analytics engine is implemented by computer readable instructions executed by a computer processor, wherein the analytics engine detects the pollution event by applying a sliding time window to a signal from the sensor, where the duration of the sliding time window is less than the duration of the signal; for each time interval captured by the sliding time window, computing a normalized standard deviation for values in the sliding time window; determining a maximum value for the normalized standard deviation across the time intervals; correlating time at which the maximum value occurs to a pollution event in the indoor setting.

13. The system of claim 12 wherein the features are selected from a group consisting of increasing rate between the peak and a first data point in the window of time, a difference between the peak and the first data point in the window of time, a decreasing rate between the peak and a last data point in the window of time, a difference between the peak and the last data point in the window of time, and a standard deviation of all data points in the window of time.

14. The system of claim 12 wherein a pollution source model in the plurality of pollution source models is defined as a Support Vector Machine.

15. The system of claim 12 further comprises a volatile organic compound sensor configured to measure concentration of organic compounds in the indoor setting, wherein the analytics engine extracts features from a signal from the volatile organic compound sensor.

16. The system of claim 12 further comprises a humidity sensor configured to measure humidity in the indoor setting, wherein the analytics engine extracts features from a signal from the humidity sensor.

17. The system of claim 12 further comprises a reporter interfaced with the analytics engine and configured to present a notification for the pollution event on a display, where the notification includes the identified source of the pollution event.

18. The system of claim 17 wherein the forecaster determines the amount of pollution using a parametric model.

19. The system of claim 17 wherein the forecaster determines the amount of pollution by comparing the pollution event to a plurality of historic pollution events, identify a given historic pollution event from the plurality of historic pollution events that correlates to the pollution event and determining an amount of pollution at the future time using the given historic pollution event.

* * * * *